(12) United States Patent
Gaeta (10) Patent No.: US 11,350,867 B2
(45) Date of Patent: Jun. 7, 2022

(54) SMALL-SCALE TIME DELAY AND SINGLE-SHOT CONDUCTION VELOCITY ANALYSIS AND MAPPING FOR CARDIAC ELECTROPHYSIOLOGY

(71) Applicant: Duke University, Durham, NC (US)

(72) Inventor: Stephen Gaeta, Durham, NC (US)

(73) Assignee: Duke University, Durham, NC (US)

( * ) Notice: Subject to any disclaimer, the term of this patent is extended or adjusted under 35 U.S.C. 154(b) by 313 days.

(21) Appl. No.: 16/397,618

(22) Filed: Apr. 29, 2019

(65) Prior Publication Data
US 2019/0328258 A1    Oct. 31, 2019

Related U.S. Application Data

(60) Provisional application No. 62/663,502, filed on Apr. 27, 2018, provisional application No. 62/666,161, filed on May 3, 2018.

(51) Int. Cl.
| | |
|---|---|
| *A61B 5/316* | (2021.01) |
| *A61B 5/25* | (2021.01) |
| *A61B 5/341* | (2021.01) |
| *A61B 5/352* | (2021.01) |
| *A61B 5/361* | (2021.01) |

(52) U.S. Cl.
CPC .............. *A61B 5/316* (2021.01); *A61B 5/25* (2021.01); *A61B 5/341* (2021.01); *A61B 5/352* (2021.01); *A61B 5/361* (2021.01)

(58) Field of Classification Search
CPC .......... A61B 5/316; A61B 5/341; A61B 5/25; A61B 5/361; A61B 5/352

USPC ........................................................ 600/509
See application file for complete search history.

(56) References Cited

U.S. PATENT DOCUMENTS

| | | | | |
|---|---|---|---|---|
| 9,131,866 | B2 * | 9/2015 | Thakur | A61B 5/287 |
| 9,510,763 | B2 * | 12/2016 | Ghosh | A61N 1/0484 |
| 9,687,167 | B2 * | 6/2017 | Laughner | A61B 5/726 |

(Continued)

OTHER PUBLICATIONS

Anter et al., "High-Resolution Mapping of Postinfarction Reentrant Ventricular Tachycardia Clinical Perspective," Circulation, 2016, 134:314-327.

(Continued)

*Primary Examiner* — Carl H Layno
*Assistant Examiner* — Michael J Lau
(74) *Attorney, Agent, or Firm* — Michael Best & Friedrich LLP (57) ABSTRACT

Systems and methods for quantifying cardiac electrophysiologic signals. An electronic processor receives a unipolar electrogram signal from each of a plurality of electrodes positioned at different locations of a heart. The electronic processor then calculates or measures a bipolar electrogram signal based on a difference between the unipolar electrogram signal for a first electrode and the unipolar electrogram signal for a second electrode. A local activation time (LAT) difference between a location of the first electrode and a local of the second electrode is then determined based on a voltage amplitude of the bipolar electrogram signal. The LAT difference is indicative of an amount of time between a local activation of a propagating wavefront at the location of the first electrode and a local activation of the propagating wavefront at the location of the second electrode.

20 Claims, 8 Drawing Sheets

(56) References Cited

U.S. PATENT DOCUMENTS

| | | | | |
|---|---|---|---|---|
| 2003/0023130 | A1* | 1/2003 | Ciaccio | A61B 5/341 600/12 |
| 2008/0208069 | A1* | 8/2008 | John | A61B 5/35 600/509 |
| 2009/0306732 | A1* | 12/2009 | Rosenberg | A61N 1/3627 607/9 |
| 2010/0049052 | A1* | 2/2010 | Sharf | G01S 7/52087 600/454 |
| 2013/0274582 | A1* | 10/2013 | Afonso | A61B 5/066 600/374 |
| 2014/0235987 | A1* | 8/2014 | Ghosh | A61B 5/361 600/374 |
| 2015/0208938 | A1* | 7/2015 | Houben | A61B 5/7203 600/509 |
| 2015/0238102 | A1* | 8/2015 | Rubinstein | A61B 5/318 600/519 |
| 2016/0120426 | A1* | 5/2016 | Urman | A61B 5/287 600/424 |
| 2017/0027463 | A1* | 2/2017 | Du | A61B 5/316 |
| 2017/0049348 | A1* | 2/2017 | Deno | A61M 25/0127 |
| 2017/0065198 | A1* | 3/2017 | Ruppersberg | A61B 5/316 |
| 2017/0172508 | A1* | 6/2017 | Huitz | A61B 5/6852 |
| 2017/0181655 | A1* | 6/2017 | El Haddad | A61B 5/7282 |
| 2017/0251942 | A1* | 9/2017 | Brodnick | A61B 5/316 |
| 2017/0281031 | A1* | 10/2017 | Houben | A61B 18/1492 |
| 2017/0354339 | A1* | 12/2017 | Zeidan | A61B 5/349 |
| 2018/0008203 | A1* | 1/2018 | Iyun | A61B 5/316 |
| 2018/0042503 | A1* | 2/2018 | Chauhan | A61B 18/1492 |
| 2018/0042505 | A1* | 2/2018 | Botzer | A61B 5/287 |

OTHER PUBLICATIONS

Bernabeu et al., "Scalable parallel preconditioners for an open source cardiac electrophysiology simulation package," Procedia Computer Science, 2011, 4:821-830.

Brunckhorst, "Ventricular mapping during atrial and ventricular pacing. Relationship of multipotential electrograms to ventricular tachycardia reentry circuits after myocardial infarction," European Heart Journal, 2002, 23:1131-1138.

Cantwell et al., A software platform for the comparative analysis of electroanatomic and imaging data including conduction velocity mapping, Conf Proc IEEE Eng Med Biol Soc, 2014, pp. 1591-1594.

Cantwell et al., "Techniques for automated local activation time annotation and conduction velocity estimation in cardiac mapping," Computers in Biology and Medicine, 2015, 65:229-242.

de Bakker et al., "Slow conduction in the infarcted human heart. "Zigzag" course of activation," Circulation, 1993, 25:1317-1323.

Deno et al., "Orientation-Independent Catheter-Based Characterization of Myocardial Activation," IEEE Trans Biomed Eng, 2017, 64:1067-1077.

Dubois et al., "Global and directional activation maps for cardiac mapping in electrophysiology," Computing in Cardiology, 2012, 39:349-352.

Ethier et al., "Semi-Implicit Time-Discretization Schemes for the Bidomain Model," SIAM J Numer Anal, 2008, 46:2443-2468.

Fitzgerald et al., "Estimation of Cardiac Conduction Velocities Using Small Data Sets," Annals of biomedical engineering, 2003, 31:250-261.

Haidar SK, Magtibay K, Porta-Sanchez A, et al.: Resolving Bipolar Electrogram Voltages During Atrial Fibrillation Using Omnipolar Mapping. Circulation: Arrhythmia and Electrophysiology American Heart Association, Inc, 2017, 10:e005018-17.

Henriquez et al., "Anisotropy, fiber curvature, and bath loading effects on activation in thin and thick cardiac tissue preparations: simulations in a three-dimensional bidomain model," J Cardiovasc Electrophysiol, 1996, 7:424-444.

Henriquez et al., "Simulation of propagation along a cylindrical bundle of cardiac tissue—I: Mathematical formulation," IEEE Trans Biomed Eng, 1990, 37:850-860.

Irie et al., "Relationship between sinus rhythm late activation zones and critical sites for scar-related ventricular tachycardia: systematic analysis of isochronal late activation mapping," Circulation: Arrhythmia and Electrophysiology American Heart Association, Inc, 2015, 8:390-399.

Jackson et al., "Decrement Evoked Potential Mapping: Basis of a Mechanistic Strategy for Ventricular Tachycardia Ablation," Circulation: Arrhythmia and Electrophysiology American Heart Association, Inc, 2015, 8:1433-1442.

Jacquemet et al., "Genesis of complex fractionated atrial electrograms in zones of slow conduction: a computer model of microfibrosis," Heart Rhythm, 2009, 6:803-810.

Jaïs et al., "Elimination of Local Abnormal Ventricular Activities: A New End Point for Substrate Modification in Patients with Scar-Related Ventricular Tachycardia," Circulation, 2012, 125(18):2184-96.

King et al., "Determinants of myocardial conduction velocity: implications for arrhythmogenesis," Front Physiol, 2013, 4:154.

Linnenbank et al., "How to measure propagation velocity in cardiac tissue: a simulation study," Front Physiol, 2014, 5:267.

Masse et al., "Resolving Myocardial Activation With Novel Omnipolar Electrograms," Circulation: Arrhythmia and Electrophysiology 2016, 9:e004107.

Nayyar et al., "High-density mapping of ventricular scar: a comparison of ventricular tachycardia (VT) supporting channels with channels that do not support VT," Circulation: Arrhythmia and Electrophysiology American Heart Association, Inc, 2014, 7:90-98.

Roney et al., An Automated Algorithm for Determining Conduction Velocity, Wavefront Direction and Origin of Focal Cardiac Arrhythmias Using a Multipolar Catheter, Conf Proc IEEE Eng Med Biol Soc, 2014, pp. 1583-1586.

Roth "Influence of a Perfusing Bath on the Foot of the Cardiac Action Potential," Circ Res American Heart Association, Inc, 2000, 86:e19-e22.

Verma et al., "Regional Conduction Velocity Calculation based on Local Activation Times: A Simulation Study on Clinical Geometries," Computing in Cardiology, 2016, vol. 43, 4 pages.

Verma et al., "Regional conduction velocity calculation from clinical multichannel electrograms in human atria," Computers in Biology and Medicine, 2018, 92:188-196.

Zheng et al., "Atrial average conduction velocity in patients with and without paroxysmal atrial fibrillation," Clinical Physiology and Functional Imaging, 2016, 37:596-601.

* cited by examiner

SMALL-SCALE TIME DELAY AND SINGLE-SHOT CONDUCTION VELOCITY ANALYSIS AND MAPPING FOR CARDIAC ELECTROPHYSIOLOGY

RELATED APPLICATIONS

This application claims the benefit of U.S. Provisional Patent Application No. 62/663,502, filed Apr. 27, 2018, entitled "SYSTEMS AND METHODS FOR SINGLE SHOT CONDUCTION VELOCITY ANALYSIS FOR CARDIAC ELECTROPHYSIOLOGY," and U.S. Provisional Patent Application No. 62/666,161, filed May 3, 2018, entitled "SYSTEMS AND METHODS FOR THE MEASUREMENT OF SMALL TIME DELAYS USING BIPOLAR VOLTAGE AMPLITUDE IN CLINICAL ELECTROPHYSIOLOGY," the entire contents of both of which are incorporated herein by reference.

BACKGROUND

The present invention relates to systems and methods for quantifying electrophysiology including, for example, cardiac electrophysiology. Cardiac electrophysiology is a clinical subspecialty of cardiology in which disorders of the rhythm of the heart (arrhythmias) are diagnosed and treated—sometimes by invasive procedures. Cardiac arrhythmia results from a complex interplay of anatomical and dynamic influences that, in many cases, remain incompletely understood and difficult to characterize clinically.

SUMMARY

In various embodiments, the invention provides systems and methods for recording electrical signal ("electrograms") from multiple locations inside and/or outside the heart using electrode catheters. In some implementations, electrical signals are processed, analyzed, and mapped onto anatomically-detailed models of a patient's heart. In this way, the sequence and characteristics of electrical activation of a patient's heart is visualized in order to better understand the arrhythmia. Anatomical locations critical for arrhythmia initiation or maintenance can be identified and targeted for subsequent ablation (i.e., tissue destruction). In some cases, the acquisition, processing, and mapping of electrograms using hardware & software systems (e.g., "electroanatomical mapping systems") that allow data visualization of electrogram features aimed at detection of clinically relevant features.

The signals recorded from each individual electrode are referred to herein as "unipolar" electrograms, in which the potential difference at the electrode is compared to a more distant, "indifferent" electrode. By subtracting a unipolar electrogram of one electrode from that of another (e.g., adjacent) electrode, a "bipolar" electrogram is calculated. In some cases, a bipolar electrogram can also be created by directly measuring the potential difference between two adjacent electrodes. Features of these bipolar electrograms can be used to guide ablation procedures. In some cases, the electrical signal of a bipolar electrogram is presumed to represent more localized electrical activity than unipolar electrograms because the electrogram is indicative of electrical activity in the local tissue under the two recording electrodes. Also, the "subtraction" used to calculate/measure a bipolar signal from two unipolar signals provides rejection of far field signals and common mode noise shared by both electrodes.

Two particular clinical features that can be derived from a bipolar electrogram that can, in some cases, be used to guide treatment include the amplitude and the timing of each electrogram. In some cases, the amplitude of each electrogram—for example, measured as the peak-to-peak amplitude of the signal (i.e., the overall voltage range spanned by the signal)—can be used as a surrogate for tissue health. For example, a high bipolar voltage may represent healthier tissue than a low (or absent) bipolar voltage and, therefore, these voltage amplitudes can be used to target ablation. The timing at each bipolar electrogram site can be annotated relative to a reference event (e.g., from a different electrode pair or a surface electrocardiogram). The annotated time at each site can be annotated in various different ways including, for example, the "activation time" at a given recording site. In some cases, the activation time at electrode site can be defined as the time at which the unipolar electrogram has its most negative slope (i.e., the maximum negative dV/dt). Local activation times can be used to quantify and analyze aspects of spatiotemporal dynamics including, for example, conduction velocity in the cardiac tissue.

Improved techniques for identification of the spatiotemporal dynamics that initiate and maintain arrhythmia will enable more patient-specific and efficacious approaches to treatment. Additionally, in clinical scenarios, it is often not possible to map electrophysiologic signals during arrhythmia without inducing the arrhythmia. Techniques for characterization of sinus or paced rhythm dynamics holds the promise of identification of pro-arrhythmic myocardial substrate without the induction of arrhythmia. Most ablation procedures are performed only with the guidance of electroanatomic maps depicting activation sequence and voltage amplitude. However, given the importance of dynamic effects on the initiation and maintenance of cardiac arrhythmia, more complex mapping approaches are likely to hold value. For example, fundamental electrodynamic and clinical studies have suggested that areas of conduction velocity (CV) deceleration are likely to be pro-arrhythmic.

Any such spatiotemporal analysis of electroanatomic maps is challenged by the fact that the maps being analyzed are themselves an approximation. To construct a map, clinically collected data is transformed multiple times, with each step introducing error to the final calculation. For example, activation maps may be influenced by errors incurred during spatial localization of electrodes, recorded chamber geometry, point projection onto the geometry, interpolation of results into a smoothed map, and ensemble averaging of data from multiple temporally different data acquisitions. When an activation map, for example, is used to identify distances and time delays between points that are then used to calculate conduction velocity (CV), any errors in the tissue map or in the activation timing data mapped onto the tissue map will be propagated (and, in some cases, magnified) in the resulting CV calculation.

In some implementations, this invention overcomes these pitfalls by providing an improved method of CV calculation using unprojected, uninterpolated data from a single acquisition period. Specifically, in some implementations, the systems and methods provided herein use a multipolar catheter to triangulate conduction velocity from many different points simultaneously using the large number of available data point combinations. In this way, conduction velocity (CV) can be calculated and mapped using measured data from a single acquisition period (e.g., a real-time single-shot CV calculation). Accordingly, sources of error prior to spatiotemporal analysis are minimized and data accuracy is improved. As used in the examples below, "acquisition period" refers to a period of time (e.g., on the order of milliseconds or hundreds of milliseconds) over which electrogram data is received from all electrodes as a single "acquisition" of data.

In one embodiment, the invention provides a method of quantifying cardiac electrophysiologic signals. An electronic processor receives a unipolar electrogram signal from each of a plurality of electrodes positioned at different locations of a heart. The electronic processor then calculates a bipolar electrogram signal based on a difference between the unipolar electrogram signal for a first electrode and the unipolar electrogram signal for a second electrode. A local activation time (LAT) difference between a location of the first electrode and a local of the second electrode is then determined based on a voltage amplitude of the bipolar electrogram signal. The LAT difference is indicative of an amount of time between a local activation of a propagating wavefront at the location of the first electrode and a local activation of the propagating wavefront at the location of the second electrode.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
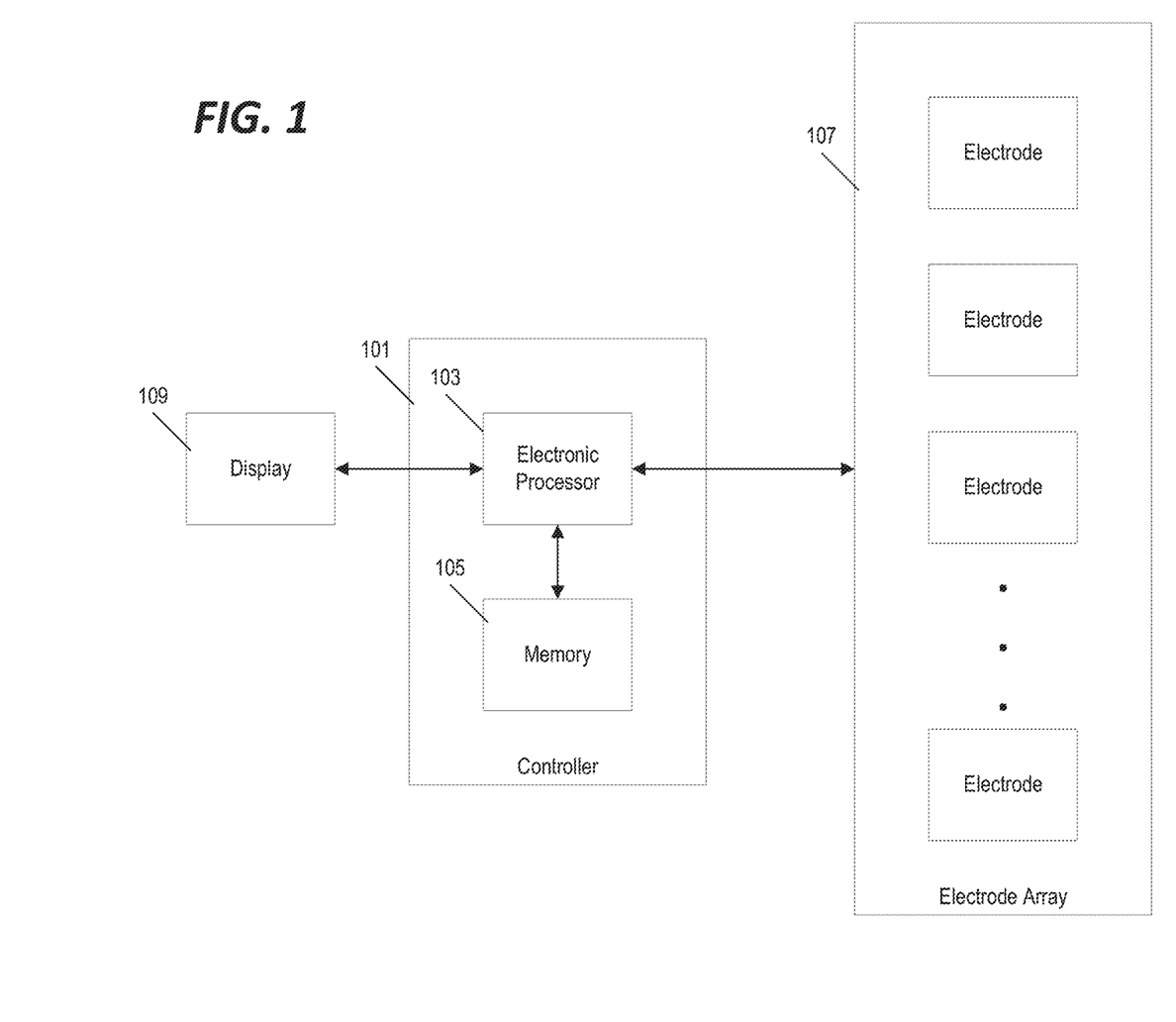
FIG. 1 is a block diagram of a system for measuring and mapping electrophysiological features according to one embodiment.

FIG. 1 illustrates an example of a system for cardiac electrophysiology measurement and analysis. The system includes a controller 101 with an electronic processor 103 and a non-transitory, computer-readable memory 105. The memory 105 stored instructions that are accessed and executed by the electronic processor 103 to provide the functionality of the controller 101 (for example, as described herein). In various implementations, the controller 101 may be provided, for example, as a desktop, laptop, or tablet computer. Although only one electronic processor and memory unit are illustrated in the example of FIG. 1, other implementations may include multiple electronic processors and/or multiple memory units provided in the same local system or distributed in other systems/locations. For example, the controller 101 might be configured to communicate through a wired or wireless interface to store and/or access data from a cloud storage.

The controller 101 is communicatively coupled to an electrode array 107 for reading and recording electrogram signals. As described further below, the electrode array 107 includes a plurality of electrodes and can be provided as a single unit (that includes multiple electrodes) or as a collection of separate electrodes (or electrode systems) that are all communicatively coupled to the controller 101. The controller 101 is also communicatively coupled to a display 109 (e.g, a LCD display unit) and is configured to cause the display 109 to output visual representations including, for example, a graphical user interface and/or graphical or numeric depictions of measured cardiac electrophysiology data.

In some implementations, the system of FIG. 1 is configured to calculate conduction velocity of a subject's heart in real-time using a multi-electrode catheter. Given the location and activation times at any three locations, the controller 101 will calculate by triangulation a CV vector that describes the propagation of a uniform planar wave travelling past the three locations. In other words, the system of FIG. 1 is configured to calculate conduction velocity (CV) using data from simultaneous acquisitions of a multipolar electrode catheter by triangulation from all available combinations of three points.

Figure 2A:
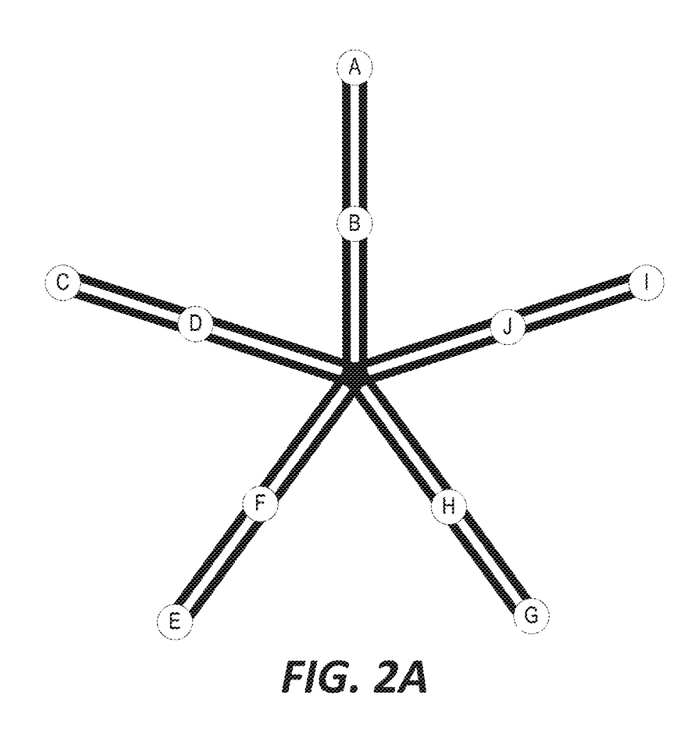
FIGS. 2A and 2B are a schematic diagrams of a multipolar catheter used in the system of FIG. 1 to simultaneously record electrogram data from multiple points on the cardiac tissue.

FIG. 2A illustrates one example of a multipolar catheter that can be used with the system of FIG. 1. The catheter of FIG. 2A includes ten electrodes (labelled A through J) arranged with two electrodes on each of five "arms" of the catheter. However, in other implementations, the multipolar catheter may include more or fewer electrodes positioned in various different arrangements (for example, more or fewer electrodes positioned on more or fewer "arms"). One commercially available example of this type of multipolar catheter is the PENTARAY catheter (Biosense Webster, Diamond Bar, Calif.). In use, the catheter is inserted towards the heart (e.g., through a blood vessel) and positioned with each electrode at a different location on or near the cardiac tissue.

Figure 2B:
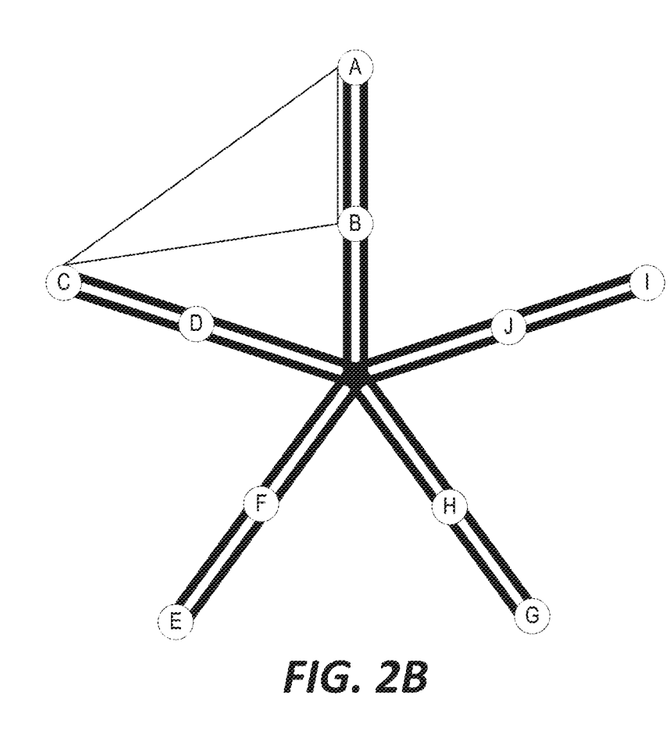

FIG. 2B illustrates an example of a combination of three electrodes of the catheter of FIG. 2A that can be used to define an area for triangulation of conduction velocity. In a catheter that includes 10 different electrodes at different positions, a total of 120 unique triangles can be defined by different electrode combinations. Also, note that triangulation can be performed with triads of LAT defined by bipolar electrograms (from three pairs of electrodes) or from triads of unipolar electrograms (from three electrodes alone).

Figure 3:
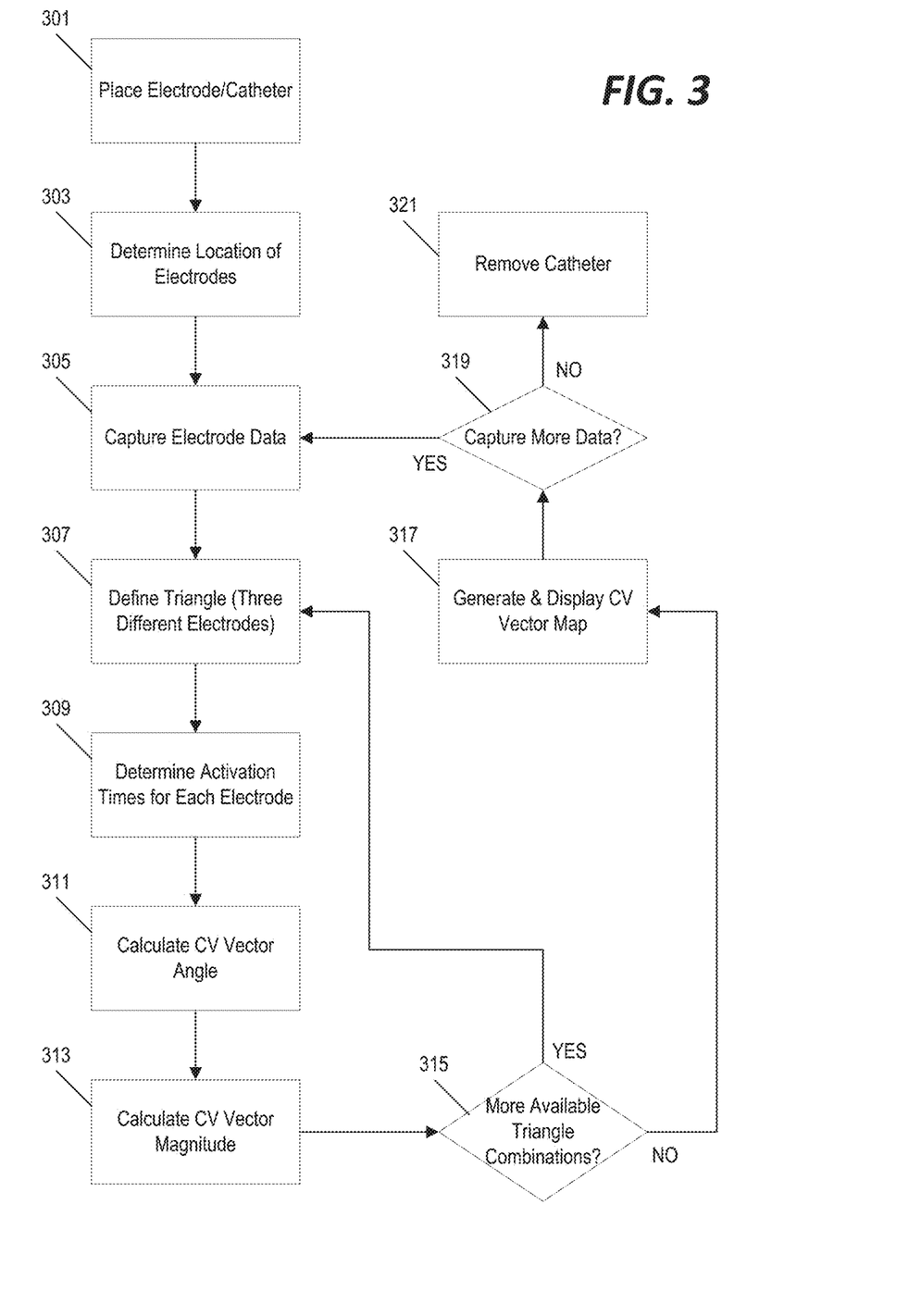
FIG. 3 is a flowchart of a method for calculating and mapping conducting velocity using the system of FIG. 1.

FIG. 3 illustrates a method for mapping conduction velocity using the system of FIG. 1 (including the catheter of FIG. 2A). First, the catheter is inserted and positioned such that each electrode is located at a different location on or near the cardiac tissue (step 301). A mapping process is applied to determine the location of each individual electrode independent from any mapping of the cardiac tissue (step 303). For example, an electromagnetic-based 3D mapping system (such as, for example, the CARTO3 system (Biosense Webster, Diamond Bar, Calif.)) can be used to determine the location of each electrode of the catheter in 3D space. Electrogram data is then recorded simultaneously from each electrode of the catheter (step 305). In some implementations, the recorded electrogram data is analyzed by the system at this point to determine a local activation time (LAT) corresponding to the location of each electrode or pair of electrodes (bipolar electrogram). In other implementations, relative activation times might be determined by comparing electrogram data from different electrodes or pairs of electrodes in each individual "triangle" combination.

After the electrogram data is captured, data for each of a plurality of different "triangles" are analyzed to determine a CV vector corresponding to each individual triangle. As described above, each "triangle" is defined as a combination of three different electrodes or three different pairs of electrodes (bipolar electrograms) of the catheter (as illustrated, for example, in FIG. 2B). After a triangle is defined/selected (step 307), the controller 101 determines an activation time for each electrode or pair of electrodes in the triangle (step 309). In some implementations, this is done by determining an absolute local activation time value for each electrode or pairs of electrodes while, in other implementations, the system determines a time delay indicative of a difference in the activation time between two specific electrodes as discussed in further detail below.

Figure 4:
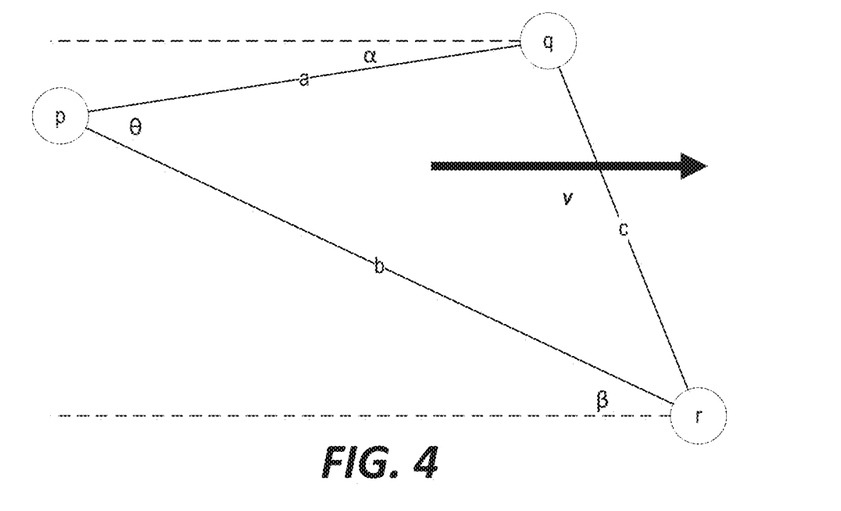
FIG. 4 is a schematic diagram of a conduction velocity vector calculated and mapped by the system of FIG. 1 for an area defined by a combination of three different electrodes of the multipolar catheter of FIGS. 2A and 2B.

The CV vector for each triangle is defined as a vector positioned in the same plane as defined by the "triangle" with its origin at the center of the triangle (the circumcenter, centroid, orthocenter, or incenter). The angular position of the CV vector (i.e., the angle from which the CV vector extends from the center in the plane defined by the triangle) is defined by the equations:

$$\theta = \cos^{-1}\left(\frac{|a|^2 + |b|^2 - |c|^2}{2|a||b|}\right) \quad (1)$$

$$\alpha = \tan^{-1}\left(\frac{t_b|a| - t_a|b| \cos \theta}{t_a|b| \sin \theta}\right) \quad (2)$$

where (as shown in FIG. 4) a, b, and c are the vectors connecting the three vertices (i.e. electrodes) of the triangle and where $t_a$ and $t_b$ are the differences in activation times at the location of the electrodes along edge a and b respectively. In other words, $t_a$ is the difference between the activation time at electrode "q" and the activation time at electrode "p" in FIG. 4 and $t_b$ is the difference between the activation time at electrode "r" and the activation time at electrode "p". As also illustrated in FIG. 4, θ is the angle between the line segment "a" and the line segment "b" where line segment "a" is a line segment extending from electrode p to electrode q and line segment "b" is a line segment extending from electrode p to electrode r. Finally, as illustrated in FIG. 4, α is the angle between line segment "a" and a line extending from electrode "q" parallel to the line of the resulting CV vector. Accordingly, a is also indicative of the angle of the determined CV vector relative to the line segment "a".

Because the system has already determined the location of each electrode in 3D space (e.g., in step 303 of FIG. 3), the magnitudes of the edge segments (a, b, and c) and the angle θ can be determined using equation (1) based on the known locations of the electrodes that define the triangle. These values, together with the activation times (or difference in activation times) as determined from the electrogram signals for each electrode or pair of electrodes making the vertices of the triangle, can then be used to determine the values $t_a$ and $t_b$ and, ultimately, the angle α using equation (2).

The magnitude v of the CV vector for each triangle can be calculated by either of the following equations:

$$v = |\alpha| \cos \alpha \quad (3)$$

For each triangle, the angle α of the CV vector represents a direction of wave propagation through the area defined by the triangle and the magnitude v of the CV vector represents the velocity of the propagating wave in that direction.

Returning to the method of FIG. 3, after a triangle is selected/identified (step 307) and both the activation times and the locations of each electrode or pairs of electrodes are determined (step 309), the system calculates the CV vector angle (step 311) using equations (1) and (2) above and calculates the CV vector magnitude (step 313) using equation (3). It is noted that, when bipole pairs are used as the vertices of the triangle combination, the center of each pair (i.e., the midway point between the two electrodes in the pair) is defined as a vertex of the triangle. The system then repeats this same process for every other available "triangle" defined by the electrodes (or electrode pairs) of the multipolar catheter (step 315). Once an angle, origin, and magnitude of a CV vector has been determined for each triangle combination, the system generates and displays a CV vector map (step 317).

Although the method of FIG. 1 illustrates the method as iteratiave—this is done primarily to illustrate an example of how the processing might be performed by an electronic processor executing software instructions. In some implementations, all available combinations of triangles are identified and CV vectors are calculated for all of the identified combinations using electrogram data that is captured over the same time period (e.g., during a single acquisition period).

Figure 5:
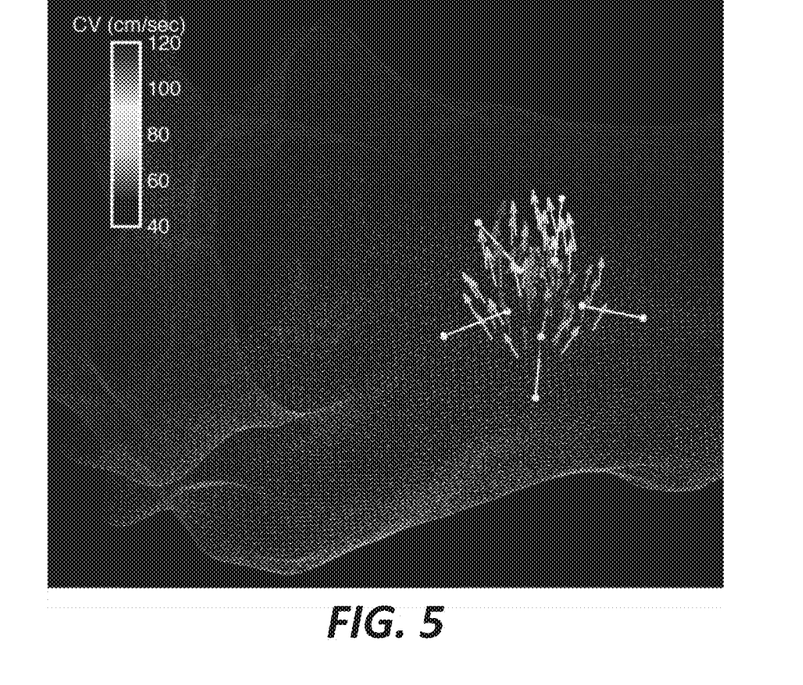
FIG. 5 is a first example of a conduction velocity map generated and displayed by the system of FIG. 1.

FIG. 5 illustrates an example of CV vectors calculated from a single acquisition of a multipolar catheter as it may be shown on the display 109 of the system of FIG. 1. The vector map includes a plurality of CV vectors (each determined for a different triangle combination of electrodes) displayed in the applicable position and orientation as determined by the method of FIG. 3. In the example of FIG. 5, the length of each displayed CV vector is indicative of the calculated magnitude for the respective vector. The example of FIG. 5 also utilizes a color-coding system in which the color of each displayed vector is also indicative of a relative magnitude calculated for the vector. This color-coding mechanism allows a user to more readily decipher relative changes in conduction velocity at different locations of the cardiac tissue based on differences in color. In the example of FIG. 5, a color scale showing the different display colors and their corresponding conduction velocity magnitudes is displayed on the left side of the image.

Also, as discussed above, in the method of FIG. 3, the position, orientation, and magnitude of each CV vector is determined based on a location of each electrode and the local activation times for each electrode. Because the CV vectors are not calculated based on any determined structure of the cardiac tissue itself, errors and variations in the mapping of the cardiac tissue are not extended to the conduction velocity mapping. However, as shown in the example of FIG. 5, in some implementations, the CV vector map is displayed as overlaid onto a graphical representation of the cardiac tissue. This overlaid display may help the user identify correlations between the measured wave propagation and the actual tissue structure of the heart. Furthermore, in some implementations, the calculated CV vectors are "applied" to the geometry of the cardiac tissue by identifying a point on the surface of the cardiac tissue closest to the origin point of the CV vector and adjusting the CV vector's position such that the origin of the CV vector is positioned at that identified closest point on the tissue surface.

Returning again to the method of FIG. 3, once a CV map is generated for a single acquisition period (step 317), the system can either capture electrode data for another subsequent acquisition period (step 319) or the process can be terminated and the catheter removed (step 321).

In some implementations, CV vectors are calculated and displayed in the CV vector map for every possible triangle combination of electrodes. However, in other implementations, various filtering mechanisms may be employed by the system to omit CV vectors or triangles that do not meet certain defined criteria. In some implementations, a CV vector may be omitted from the CV map if the velocity (i.e., the magnitude v of the vector) is an outlier—for example, if the calculated vector magnitude is more than three standard deviations from a median vector magnitude amongst all CV vectors for the entire map. In some implementations, a CV vector may be omitted from the CV map if a difference between the vector angle α and a mean angle of acquisition is more than a threshold (e.g., 70 degrees). In some implementations, a CV vector is omitted for a triangle if the difference between the activation times for two electrodes in the triangle is not greater than a threshold (e.g., if there is no detectable and/or significant difference in the local activation times). In some implementations, a CV vector is omitted from the CV map if the ratio of the circumcircle area of the triangle relative to the area of the triangle itself is less than a threshold (e.g., 10) in order to avoid long, narrow triangles. In some implementations, the controller is configured to first determine whether a CV vector for a particular triangle combination would be omitted from the CV map based on the triangle itself or the determined activation times before calculating the CV vector. In such combinations, if the CV vector would be omitted from the CV map regardless of the angle or magnitude of the CV vector, then the controller does not calculate a CV vector for that particular triangle combination.

Figure 6A:
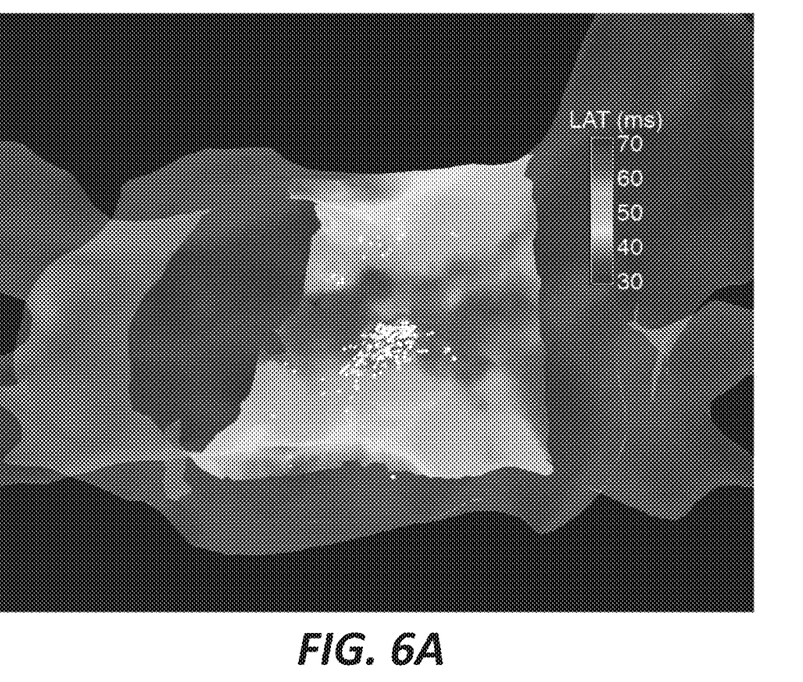
FIG. 6A is an example of a local activation time map generated and displayed by the system of FIG. 1.
Figure 6B:
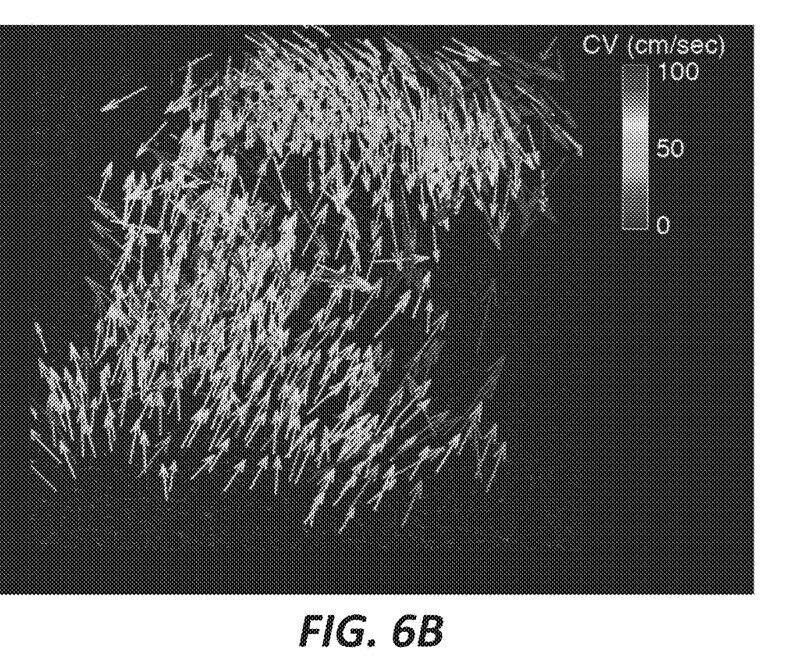
FIG. 6B is an example of a conduction velocity map generated and displayed by the system of FIG. 1 and corresponding to the local activation time map of FIG. 6A.

As discussed above, in some implementations, the system of FIG. 1 can be configured to display other graphical and/or textual information derived from the electrogram data in addition to the CV map. For example, FIG. 6A illustrates an example of a color-coded map of local activation times (LAT) in which activation times at various locations are displayed as a gradient. In some implementations, the system of FIG. 1 may be configured to generate and display a LAT map like the one illustrated in FIG. 6A. FIG. 6B illustrates an example of a CV map corresponding to the LAT map of FIG. 6A. The system of FIG. 1 may be configured to display the LAT map and the CV map concurrently (e.g., on the display at the same time) and/or may include a function to toggle between the two maps automatically or in response to a user input.

FIGS. 6A and 6B illustrate an example of a wavefront collision in which waveforms propagating across the cardiac tissue collide at the center of the left atrial posterior wall (LAPW). The CV map of FIG. 6B allows for visualization of the direction and speed of both advancing wavefronts. As discussed above, CV vectors are not included in this CV map if there is no significant difference between the activation times of two electrodes in the triangle combination. This is reflected visually in the example of FIG. 6B in which fewer CV vectors are calculated/displayed in the zone of collision due to insufficient activation time differences between electrode points. Interpolation of the CV vectors through this zone gives the appearance of slower conduction velocity due to interpolation between wavefronts with opposite directions. The white dots in FIG. 6A represent areas where the calculated CV vectors (which are not shown at these sites) have high variance from the mean of their acquisition. These "dots" may be useful to identify areas of wavefront collisions or other clinically relevant phenomena.

As illustrated in the examples above, conduction velocity mapping can be used to provide a visual indication of both speed and direction of wave propagation. It can also be used to identify areas to be targeted for ablation, as clinical studies have suggested that areas in which conduction velocity decreases are likely to be pro-arrhythmic. However, because the CV vectors are calculated based on a determined position of the electrodes and local activation time (LAT) differences, the accuracy of these CV mapping techniques (and other electrophysiology measurement/analysis techniques) can be dependent on the spatial accuracy of distance measurements and the temporal accuracy of location activation time (LAT) differences.

Local activation timing (LAT) can be defined as the time at which a unipolar electrogram has its most negative slope (i.e., the maximum negative dV/dt). However, the temporal resolution of LAT annotations can, in some systems, be 1.0 ms or higher (i.e., with a 1 kHz sampling rate). This temporal resolution may be insufficient for measurement of timing differences between very closely spaced electrodes (e.g., it may be impossible to detect a timing difference in the maximum negative dV/dt in electrograms from two closely spaced electrodes). For example, if the conduction velocity is 80 cm/sec, the LAT difference for a pair of electrodes that are separated by 1 mm would be 1.25 ms. If the system is unable to accurately resolve below 1.0 ms, this LAT difference cannot be accurately quantified.

Figure 7:
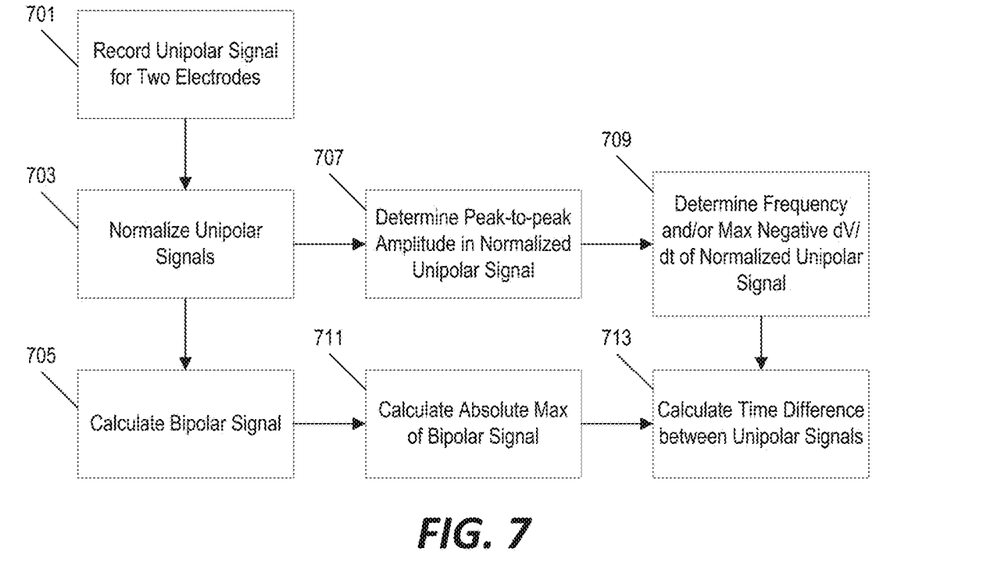
FIG. 7 is a flowchart of a method for calculating an activation time difference between two electrodes based on bipolar voltage using the system of FIG. 1.

FIG. 7 illustrates a method for measuring small LAT differences to enable accurate CV calculation from closely spaced electrodes. This method may be referred to as "Determination of Electrogram Latencies by Transformation of Amplitude" (DELTA) and derives the LAT difference between a pair of electrodes from the peak voltage amplitude of the bipolar electrogram between the two electrodes. Through this technique, measurements of timing differences are determined based on data recorded in the more finely sampled voltage domain and, thereby, provides a resolution of LAT differences that can be below the data sampling rate.

Figure 8A:
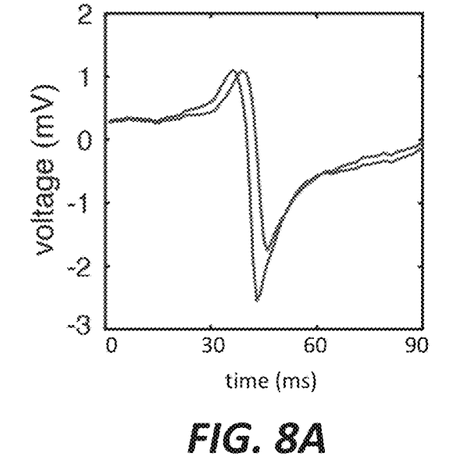
FIG. 8A is a graph of two unipolar signals measured by the system of FIG. 1.
Figure 8B:
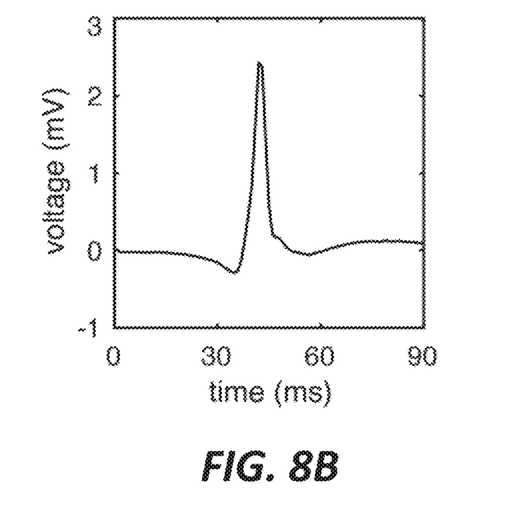
FIG. 8B is a graph of a bipolar signal generated from the two unipolar signals of FIG. 8A.
Figure 8C:
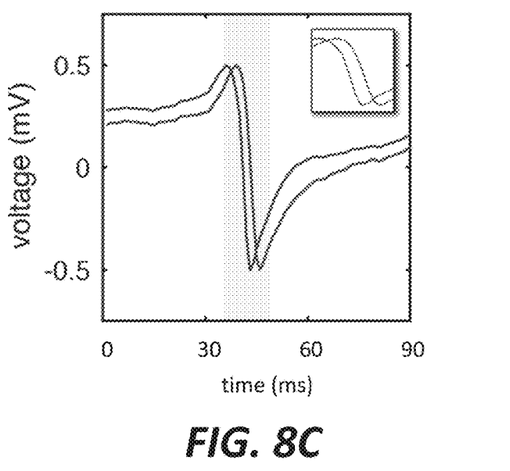
FIG. 8C is a graph of the two unipolar signals of FIG. 8A after amplitude normalization.

The method of FIG. 7 begins with unipolar signals recorded from two different electrodes (step 701). An example of unipolar electrograms recorded from two different electrodes is illustrated in FIG. 8A. In some implementations, the recorded unipolar signal are normalized to the same peak-to-peak voltage range (step 703). In some implementations, if the electrodes spacing is sufficiently small, the system can be configured to assume equal amplitude and normalization is not necessary. In various implementations, the system may be configured to measure a baseline voltage amplitude for normalization using (1) the entire unipolar signal or (2) a smaller window of each unipolar signal, for example, surround the period of its downstroke. FIG. 8C illustrates an example of the two unipolar signals of FIG. 8A after amplitude normalization.

Figure 8D:
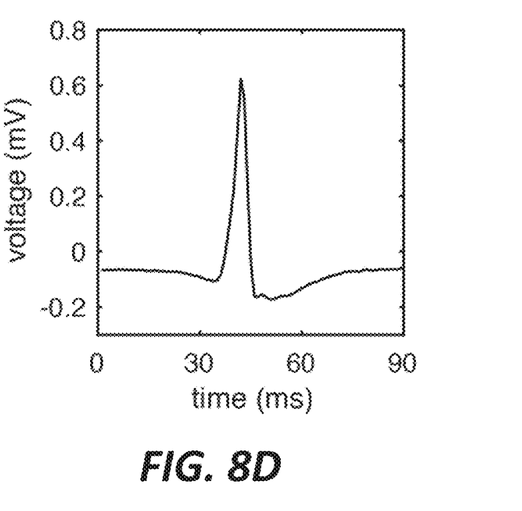
FIG. 8D is a graph of a bipolar signal generated from the amplitude normalized unipolar signals of FIG. 8C.

The system then calculates a bipolar voltage by subtracting the unipolar electrogram of one electrode from that of the other using, for example, analog circuitry or digital computation after analog-to-digital conversion of the unipolar signals (step 705). FIG. 8B illustrates an example of the bipolar electrogram calculated based on the difference between the original unipolar electrograms of FIG. 8A. FIG. 8D illustrates an example of the bipolar electrogram calculated from the amplitude-normalized unipolar electrograms of FIG. 8C. Although FIGS. 8C and 8D illustrate amplitude normalization, in some implementations, other normalization techiniques might be applied to the unipolar signals in addition to or instead of amplitude normalization. For example, the controller may be configured to normalize two unipolar signals based on the maximum negative dV/dt (i.e., the steepest point on the downstroke of the unipolar signal).

Figure 9A:
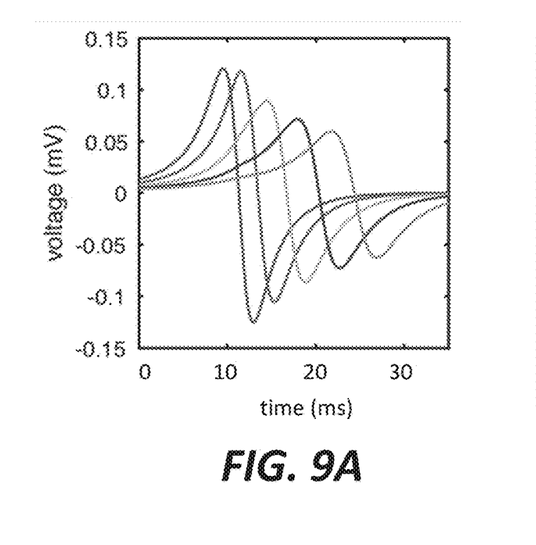
FIG. 9A is a graph of an example of unipolar electrogram signals measured simultaneously at five different electrode sites using the system of FIG. 1.
Figure 9B:
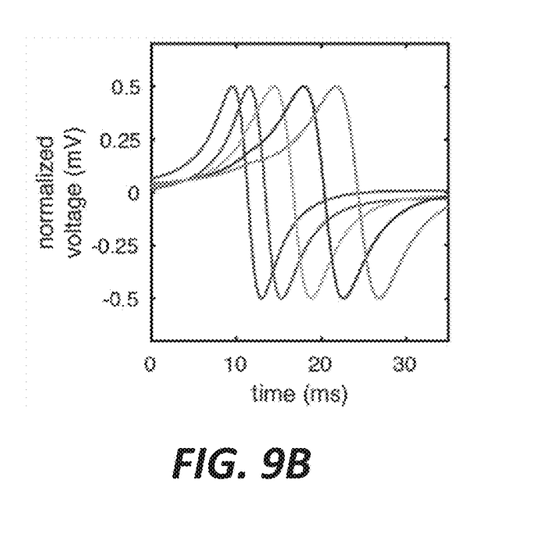
FIG. 9B is a graph of the unipolar electrogram signals of FIG. 9A after normalization.

From the normalized (or original) unipolar electrograms, the system determines a peak-to-peak amplitude of the unipolar electrogram signals (U) (step 707). The system also determines a frequency ($\omega$) of the unipolar signals and/or the maximum negative dV/dt (m) (step 709). In some implementations, the system may be configured to apply a curve fitting routine to define a mathematical function that represents the unipolar signal of one or both of the electrodes. In such implementations, the frequency ($\omega$) and the maximum negative dV/dt (m) can be determined by the system based on the mathematical function. This mathematical "curve fitting" can also be used in some implementations for a more complete normalization of the unipolar signals. For example, FIG. 9A shows a graph of the unipolar signals from five different electrodes. By applying a curve-fitting technique to determine a mathematical function that best represents the unipolar signal of all five electrodes, the signals can be normalized as shown in FIG. 9B so that the unipolar signals are each represented as the same mathematically defined function with a temporal offset. However, in other implementations, the system may be configured to measure the frequency ($\omega$) and/or the maximum negative dV/dt (m) directly from the normalized (or original) unipolar signals instead of using a mathematical approximation of the function to calculate those values.

From the bipolar electrogram, the system determines an absolute maximum of the bipolar signal (B) (i.e, the positive or negative peak with the greatest absolute value) (step 711). The peak voltage amplitude of this bipolar electrogram quantitatively encodes the LAT difference between its component unipolar signals. The system then calculates the LAT difference between the locations corresponding to the two electrodes based on the absolute maximum of the bipolar signal (B), the peak-to-peak amplitude of the unipolar signals (U), and either the frequency ($\omega$) or the maximum negative dV/dt (m) for the unipolar signal (step 713).

The phase difference ($\phi$) between the unipolar signals of the two different electrodes can be calculated using the measured bipolar amplitude (B) and the peak-to-peak amplitude of the unipolar signals (U) by the equation:

$$\varphi = 2 \sin^{-1} \frac{B}{U} \tag{4}$$

As discussed above, U can be measured from the unipolar signals or will already be known if the signals have previously been normalized to a known peak-to-peak amplitude. If the two unipolar signals have different measured amplitudes (e.g., in the case of non-normalized signals), this calculation can be performed with U set to the average of the two, the smaller of the two, or the greater of the two. Alternatively, the phase difference can be approximated by the equation:

$$\varphi = \frac{2B}{U} \tag{5}$$

As also discussed above in reference to FIG. 7, the LAT difference can be calculated using either the frequency ($\omega$) or the maximum negative dV/dt (m) for the unipolar signal. These values can be determined using analog circuitry or digitally (after digital conversion). Also, as for U (above), if these values differ between the two unipolar signals, the calculations below can be performed with the minimum, maximum, or mean of these values from the two unipolar signals. Alternatively, the LAT difference can be calculated multiple times using values from each of the unipolar signals and then averaged to provide a final determined LAT difference value.

If the system is configured to determine a frequency of the unipolar downstrokes, then the LAT difference (t) between the two electrodes can be calculated, for example, by either of the two following equations:

$$\tau = \frac{-2}{\omega} \sin^{-1} \frac{B}{U} \tag{6}$$

$$\tau = \frac{-2B}{\omega U} \tag{7}$$

If the system is configured to determine a maximum negative dV/dt (m) of the unipolar signals, then the LAT difference ($\tau$) between the two electrodes can be calculated, for example, by either of the two following equations:

$$\tau = \frac{U}{m} \sin^{-1} \frac{B}{U} \tag{8}$$

$$\tau = \frac{B}{m} \tag{9}$$

The techniques discussed above for determining LAT differences can be further extended to determine absolute activation times relative to a reference. For example, if the LAT of a first electrode is X and the LAT difference between the first electrode and a second electrode is $\tau$, then the LAT for the second electrode is X+$\tau$. Similarly, if the LAT difference between electrode 1 and electrode 2 is Y and the LAT difference between electrode 1 and electrode 3 is Z, then the LAT difference between electrode 2 and electrode 3 might be determined as the difference between Y and Z.

Figure 10:
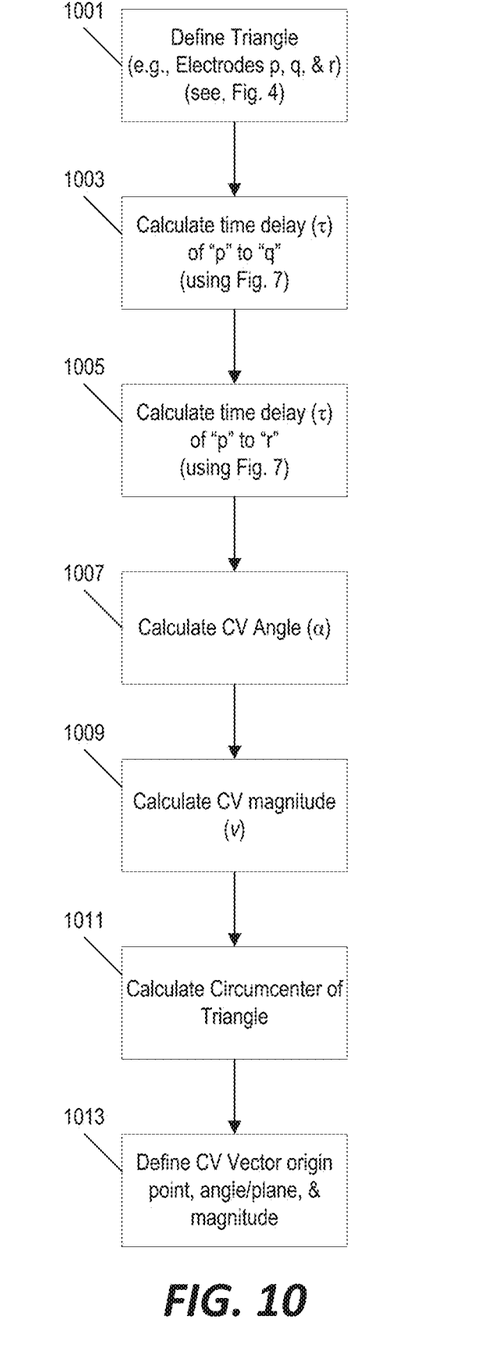
FIG. 10 is a flowchart of a method for determining a conduction velocity (CV) vector for an area defined by three electrodes using the system of FIG. 1 and the method of FIG. 7 for calculating activation time delays based on bipolar voltage.

Furthermore, this technique for measuring and quantifying LAT differences based on the maximum voltage of a bipolar signal can be further used to determine the conduction velocity and the CV mapping as discussed above in reference to FIG. 3. FIG. 10 illustrates a method for defining a CV vector for a triangle combination of three electrodes using the LAT differences method of FIG. 7.

After a "triangle" combination of three electrodes is identified or selected (step 1001) (see, e.g., FIG. 4), the method of FIG. 7 is used to calculate an LAT difference between electrode "p" and electrode "q" (i.e., $t_a$) (step 1005). The method of FIG. 7 is also used to calculate an LAT difference between the electrode "p" and the electrode "r" (i.e., $t_b$) (step 1005). The system then calculates a CV vector angle (a) for the triangle combination using equations (1) and (2) (above) (step 1007) and calculates the CV magnitude (v) using equation (3). The center of the triangle (with various definitions as above) defined by the locations of the three electrodes is then calculated (step 1011) and the CV vector for the triangle combination is defined as a vector originating from the center of the triangle, extending in the plane defined by the triangle at an angle α relative to an edge of the triangle, and with a magnitude (v) (step 1013).

Thus, the invention provides, among other things, systems and methods for determining a local activation time difference between two cardiac electrodes based on the bipolar voltage amplitude and for characterizing conduction velocity using single-shot electrogram data (i.e., electrogram data from a single acquisition period). Additional features and advantages of the invention are set forth in the following claims.

What is claimed is:

1. A method of quantifying cardiac electrophysiologic signals, the method comprising: receiving, by an electronic processor, a unipolar electrogram signal from each of a plurality of electrodes, each electrodes of the plurality of electrodes positioned at a different location of a heart, the plurality of electrodes including a first electrode, a second electrode, and a third electrode; calculating, by the electronic processor, a first bipolar electrogram signal based on a difference between a unipolar electrogram signal for the first electrode and a unipolar electrogram signal for the second electrode; calculating, by the electronic processor, a second bipolar electrogram signal based on a difference between the unipolar electrogram signal for the first electrode and a unipolar electrogram signal for the third electrode; calculating, by the electronic processor, a third bipolar electrogram signal based on a difference between the unipolar electrogram signal for the second electrode and the unipolar electrogram signal for the third electrode; determining, by the electronic processor, a first local activation time difference based at least in part on a determined value of an absolute maximum voltage amplitude of the first bipolar electrogram signal, wherein the first local activation time difference is an amount of time between a local activation of a propagating wavefront at the location of the first electrode and a local activation of the propagating wavefront at the location of the second electrode; determining, by the electronic processor, a second local activation time difference based on a determined value of an absolute maximum voltage amplitude of the second bipolar electrogram signal; determining, by the electronic processor, a third local activation time difference based on a determined value of an absolute maximum voltage amplitude of the third bipolar electrogram signal; determining a plurality of conduction velocity vectors, wherein the plurality of conduction velocity vectors includes a first conduction velocity vector for a first group of electrodes including the first electrode, the second electrode, and the third electrode based on the first local activation time difference, the second activation time difference, and the third activation time difference, and a second conduction velocity vector for an additional group of electrodes of the plurality of electrodes, wherein the additional group of electrodes includes at least one electrode that is not included in the first group of electrodes; generating a conduction velocity map indicative of relative conduction velocity of the propagating wavefront based on the plurality of conduction velocity vectors, the plurality of conduction velocity vectors including a different conduction velocity vector for each of a plurality of different electrode groups of the plurality of electrodes; and displaying the conduction velocity map on a display screen.

2. The method of claim 1, further comprising determining a maximum negative slope of one or both of the unipolar electrogram signal for the first electrode and the unipolar electrogram signal for the second electrode, wherein determining the local activation time difference includes determining the local activation time difference based on the determined value of the absolute maximum voltage amplitude of the bipolar electrogram signal and a determined value of the maximum negative slope of the unipolar electrogram signal.

3. The method of claim 2, wherein determining the local activation time difference includes determining the local activation time difference using the equation $$\tau = \frac{B}{m}$$

where T is the local activation time difference, B is the absolute maximum voltage of the bipolar electrogram signal, and m is the maximum negative slope of the unipolar electrogram signals.

4. The method of claim 1, wherein determining the local activation time difference includes determining the local activation time difference using the equation $$\tau = \frac{U}{m}\sin^{-1}\frac{B}{U}$$

where τ is the local activation time difference, U is a peak-to-peak amplitude of the unipolar electrogram signal, B is the absolute maximum voltage of the bipolar electrogram signal, and m is the maximum negative slope of the unipolar electrogram signals.

5. The method of claim 1, further comprising normalizing an amplitude of the unipolar electrogram signal for the first electrode and an amplitude of the unipolar electrogram signal for the second electrode, and wherein calculating the bipolar electrogram signal includes calculating the bipolar electrogram signal as a difference between the amplitude-normalized unipolar electrogram signal for the first electrode and the amplitude-normalized unipolar electrogram signal for the second electrode.

6. The method of claim 1, further comprising:
identifying, by the electronic processor, a plurality of triangle combinations each including three electrodes of the plurality of electrodes, wherein the plurality of triangle combinations includes a first triangle combination including the first electrode, the second electrode, and the third electrode; and calculating a conduction velocity vector for each triangle combination of the plurality of triangle combinations.

7. The method of claim 6, wherein calculating the conduction velocity vector for each triangle combination includes determining a location in three-dimensional space of each electrode of the triangle combination, determining local activation time differences between the locations of the three electrodes in the triangle combination based at least in part on a voltage amplitude of a bipolar electrogram signals calculated based on differences between the unipolar electrogram signals for the electrodes of the triangle combination, and calculating a conduction velocity vector angle and a conduction velocity vector magnitude based at least in part on the local activation time differences, wherein the conduction velocity vector angle is indicative of a direction of wave propagation in an area defined by a triangle formed by the three electrodes in the triangle combination, and wherein the conduction velocity magnitude is indicative of a speed of the wave propagation in the direction of the conduction velocity vector angle.

8. The method of claim 6, wherein calculating the conduction velocity vector for each triangle combination of the plurality of triangle combinations includes defining a conduction velocity vector with an origin positioned at a center of a triangle formed by the three electrodes in the triangle combination, wherein the conduction velocity vector extends from the center of the triangle in a plane defined by the triangle and at a vector angle relative to one edge of the triangle, and wherein the vector angle and a magnitude of the conduction velocity vector is determined based at least in part on the determined local activation time difference for electrodes in the triangle combination.

9. The method of claim 6, wherein calculating the conduction velocity vector for each triangle combination of the plurality of triangle combinations includes calculating the conduction velocity vector for each triangle combination based on electrogram data recorded for only a single acquisition period.

10. The method of claim 6, wherein calculating the conduction velocity vector for each triangle combination of the plurality of triangle combinations includes calculating the conduction velocity vector based only on a determined location of each electrode of the plurality of electrodes and electrogram data recorded by the electrodes.

11. The method of claim 6, further comprising generating a conduction velocity map including a visual representation of the conduction velocity vector calculated for each triangle combination of the plurality of triangle combinations, and wherein the conduction velocity vectors of the vector map are not calculated based on a separate three-dimensional representation of cardiac tissue.

12. The method of claim 1, wherein determining the local activation time difference between the location of the first electrode and the location of the second electrode includes determining the local activation time difference without determining a local activation time at the location of the first electrode or the local activation time at the location of the second electrode.

13. The method of claim 1, wherein generating the conduction velocity map includes generating the conduction velocity map using electrogram data only from a single data acquisition period.

14. A system for quantifying cardiac electrophysiologic signals, the system comprising: a controller configured to receive a unipolar electrogram signal from each of a plurality of electrodes, each electrode of the plurality of electrodes positioned at a different location of a heart, the plurality of electrodes including a first electrode, a second electrode, and a third electrode, calculate a first bipolar electrogram signal, based on a difference between a unipolar electrogram signal for the first electrode and a unipolar electrogram signal for the second electrode calculate a second bipolar electrogram signal based on a difference between the unipolar electrogram signal for the first electrode and a unipolar electrogram signal for the third electrode, calculate a third bipolar electrogram signal based on a difference between the unipolar electrogram signal for the second electrode and the unipolar electrogram signal for the third electrode, determine a first local activation time difference based at least in part on a value of an absolute maximum voltage amplitude of the first bipolar electrogram signal, wherein the local activation time difference is an amount of time between a local activation of a propagating wavefront at the location of the first electrode and a local activation time of the propagating wavefront at the location of the second electrode, determine a second local activation time difference based on a determined value of an absolute maximum voltage amplitude of the second bipolar electrogram signal; determine a third local activation time difference based on a determined value of an absolute maximum voltage amplitude of the third bipolar electrogram signal; determine a plurality of conduction velocity vectors, wherein the plurality of conduction velocity vectors includes a first conduction velocity vector for a group of electrodes including the first electrode, the second electrode, and the third electrode based on the first local activation time difference, the second activation time difference, and the third activation time difference; and a second conduction velocity vector for an additional group of electrodes of the plurality of electrodes, wherein the additional group of electrodes includes at least one electrode that is not included in the first group of electrodes; generate a conduction velocity map indicative of relative conduction velocity of the propagating wavefront based on the plurality of conduction velocity vectors, the plurality of conduction velocity vectors including a different conduction velocity vector for each of a plurality of different electrode groups of the plurality of electrodes; and display the conduction velocity map on a display screen.

15. The system of claim 14, wherein the controller is configured to determine a maximum negative slope of one or both of the unipolar electrogram signal for the first electrode and the unipolar electrogram signal for the second electrode, and wherein the controller is configured to determine the local activation time difference by determining the local activation time difference based on the value of the absolute maximum voltage amplitude of the bipolar electrogram signal and a value of the maximum negative slope of the unipolar electrogram signal.

16. The system of claim 15, wherein the controller is configured to determine the local activation time difference by determining the local activation time difference using the equation $$\tau = \frac{B}{m}$$

where $\tau$ is the local activation time difference, B is the absolute maximum voltage of the bipolar electrogram signal, and m is the maximum negative slope of the unipolar electrogram signals.

17. The system of claim 15, wherein the controller is configured to determine the local activation time difference by determining the local activation time difference using the equation $$\tau = \frac{U}{m}\sin^{-1}\frac{B}{U}$$

where $\tau$ is the local activation time difference, U is a peak-to-peak amplitude of the unipolar electrogram signal, B is the absolute maximum voltage of the bipolar electrogram signal, and m is the maximum negative slope of the unipolar electrogram signals.

18. The system of claim 13, wherein the controller is further configured to normalize an amplitude of the unipolar electrogram signal for the first electrode and an amplitude of the unipolar electrogram signal for the second electrode, and
wherein the controller is configured to calculate the bipolar electrogram signal by calculating the bipolar electrogram signal as a difference between the amplitude-normalized unipolar electrogram signal for the first electrode and the amplitude-normalized unipolar electrogram signal for the second electrode.

19. The system of claim 14, wherein the controller is configured to determine the local activation time different between the location of the first electrode and the location of the second electrode by determining the local activation time difference without determining a local activation time at the location of the first electrode or the local activation time at the location of the second electrode.

20. The system of claim 14, wherein the controller is configured to generate the conduction velocity map by generating the conduction velocity map using electrogram data only from a single data acquisition period.

\* \* \* \* \*